(12) United States Patent
Imamura et al.

(10) Patent No.: US 9,782,146 B2
(45) Date of Patent: Oct. 10, 2017

(54) ULTRASONIC DIAGNOSTIC SCANNER AND METHOD FOR PROCESSING ULTRASONIC SIGNAL

(75) Inventors: Tomohisa Imamura, Nasushiobara (JP); Tetsuya Kawagishi, Nasushiobara (JP); Fumiyasu Sakaguchi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 504 days.

(21) Appl. No.: 11/562,234

(22) Filed: Nov. 21, 2006

(65) Prior Publication Data

US 2007/0167780 A1    Jul. 19, 2007

(30) Foreign Application Priority Data

Nov. 25, 2005 (JP) ................. 2005-340429
Mar. 10, 2006 (JP) ................. 2006-065425

(51) Int. Cl.
*A61B 8/00* (2006.01)
*A61B 8/08* (2006.01)
(Continued)

(52) U.S. Cl.
CPC .............. *A61B 8/00* (2013.01); *A61B 8/5207* (2013.01); *G01S 7/52038* (2013.01);
(Continued)

(58) Field of Classification Search
CPC ............. G01S 7/52038; G01S 15/8963; G01S 15/8977; A61B 8/00; A61B 8/5207
(Continued)

(56) References Cited

U.S. PATENT DOCUMENTS 6,440,075 B1 *   8/2002   Averkiou ................ 600/443
6,679,846 B2 *   1/2004   Napolitano et al. ........ 600/447
(Continued)

FOREIGN PATENT DOCUMENTS

JP     8-336527     12/1996
JP    10-179589      7/1998
(Continued)

OTHER PUBLICATIONS

U.S. Appl. No. 11/924,147, filed Oct. 25, 2007, Kawagishi, et al.
(Continued)

*Primary Examiner* — Jonathan Cwern
(74) *Attorney, Agent, or Firm* — Oblon, McClelland, Maier & Neustadt, L.L.P.

(57) ABSTRACT

An ultrasonic diagnostic scanner is provided which includes a transmitting and receiving unit that transmits two kinds of ultrasonic waves with inverted phases to each of a plurality of scanning lines and receives first and second echo signals corresponding to the two kinds of ultrasonic waves from one scanning line to another, a first adder that obtains a third echo signal by adding up the first and second echo signals for each scanning line, a first signal generating unit that generates a first processed signal from the first echo signal and a second processed signal from the third echo signal, a second adder that generates a third processed signal from the first and second processed signals, an image processor that generates an ultrasonic image from the third processed signal, and an display monitor that displays the ultrasonic image.

4 Claims, 11 Drawing Sheets

(51) Int. Cl.
*G01S 7/52* (2006.01)
*G01S 15/89* (2006.01)
*G01S 15/10* (2006.01)

(52) U.S. Cl.
CPC ......... *G01S 15/8963* (2013.01); *G01S 15/104* (2013.01); *G01S 15/8977* (2013.01)

(58) Field of Classification Search
USPC ................................ 600/442–443, 451, 458
See application file for complete search history.

(56) References Cited

U.S. PATENT DOCUMENTS

| | | | |
|---|---|---|---|
| 6,705,996 | B2 | 3/2004 | Kawagishi et al. |
| 2003/0187354 | A1* | 10/2003 | Rust et al. .................... 600/437 |
| 2004/0254462 | A1 | 12/2004 | Kawagishi et al. |
| 2005/0256404 | A1* | 11/2005 | Sato .............................. 600/437 |
| 2007/0083109 | A1* | 4/2007 | Ustuner et al. ............... 600/437 |

FOREIGN PATENT DOCUMENTS

| | | |
|---|---|---|
| JP | 2001-8933 | 1/2001 |
| JP | 2001-61841 A | 3/2001 |
| JP | 2001-112754 | 4/2001 |
| JP | 2002-11004 | 1/2002 |
| JP | 2002-301068 | 10/2002 |
| JP | 2002-537048 | 11/2002 |
| JP | 2004-208918 | 7/2004 |
| JP | 2004-222824 | 8/2004 |
| JP | 2004-298620 | 10/2004 |

OTHER PUBLICATIONS

Final Notice of Rejection issued Aug. 23, 2011 in Japanese Patent Application No. 2006-065425 (with English translation).
Japanese Office Action issued Dec. 20, 2011, in Patent Application No. 2006-286981 (with English-language translation).
Japanese Office Action Issued Dec. 4, 2012 in Patent Application No. 2012-034377 (with English translation).
Office Action issued Oct. 22, 2013, in Japanese Patent Application No. 2012-004396 with English translation.
Iwao Abiru, et al., "Nonlinear Propagation of Pulsed Ultrasound", Shingakugihou, US 89-23, pp. 53-60.

* cited by examiner

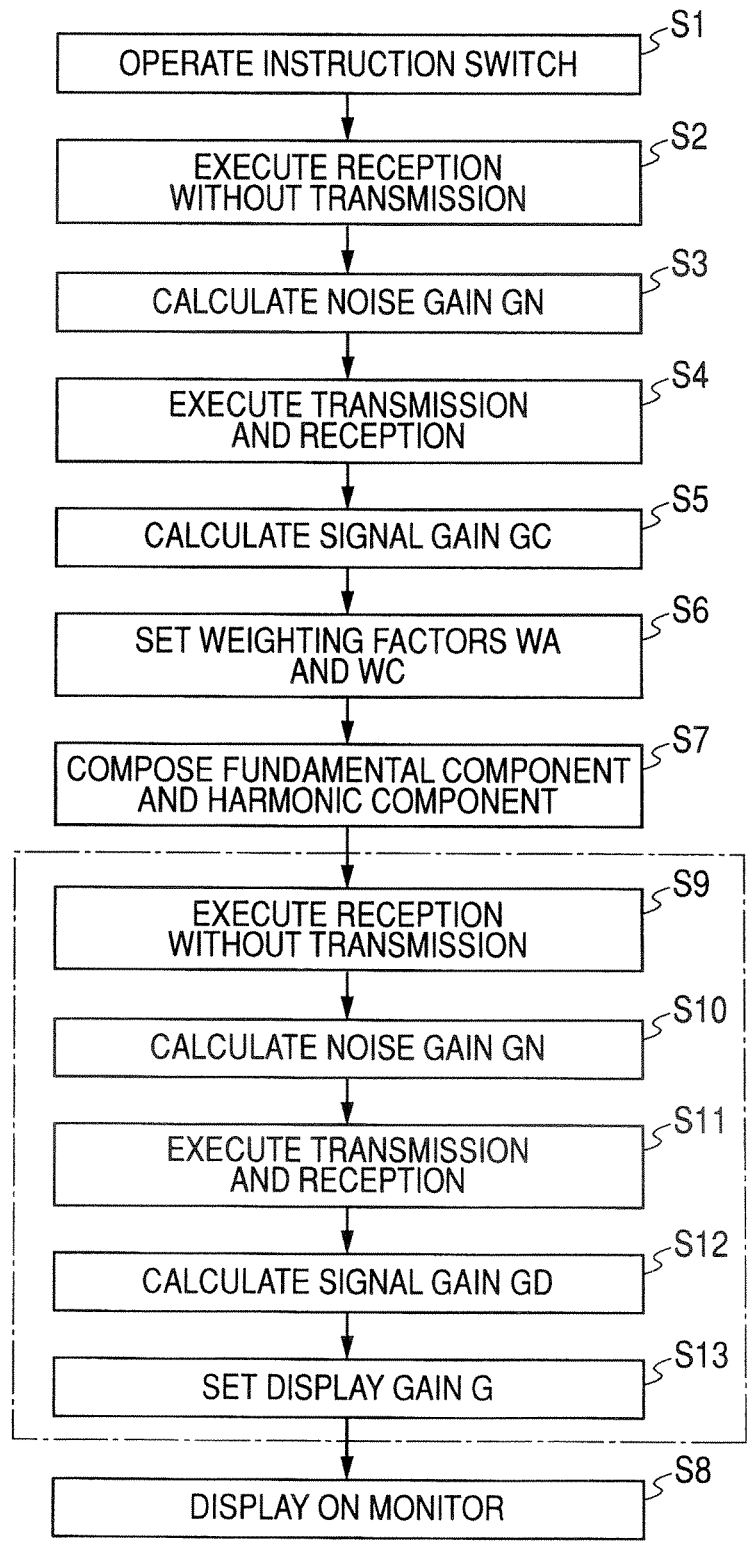

FIG. 17

| INTERSECTING POINT P | TRANSMISSION FREQUENCY | RECEPTION FREQUENCY | DISPLAY DEPTH | DYNAMIC RANGE |
|---|---|---|---|---|
| 5 cm OR LESS | 2 MHz | 2 MHz | 10 cm | 50 dB |
| 5 cm TO 10 cm | 3 MHz | 3 MHz | 15 cm | 55 dB |
| 10 cm TO 15 cm | 4 MHz | 4 MHz | 20 cm | 60 dB |
| 15 cm TO 20 cm | 5 MHz | 5 MHz | 25 cm | 65 dB |
| 20 cm TO 25 cm | 6 MHz | 6 MHz | 30 cm | 70 dB |

ULTRASONIC DIAGNOSTIC SCANNER AND METHOD FOR PROCESSING ULTRASONIC SIGNAL

CROSS-REFERENCE TO RELATED APPLICATIONS

This application is based upon and claims the benefit of priority from prior Japanese Patent Applications No. 2005-340429, filed Nov. 25, 2005; and No. 2006-065425, filed Mar. 10, 2006, the entire contents of both of which are incorporated herein by reference.

BACKGROUND OF THE INVENTION

1. Field of the Invention

The present invention relates to an ultrasonic diagnostic scanner which extracts a harmonic component caused by ultrasonic nonlinear propagation in biological tissues to image the cross section of the biological tissues.

2. Description of the Related Art

Known diagnostic ultrasonography has often used a technique of imaging the cross section of biological tissues using a fundamental contained in echo signals from the biological tissues. However, the technique of using the fundamental of echo signals often generates artifacts, thus producing the problem of decreasing the quality of the diagnostic images.

Accordingly, tissue harmonic imaging has recently been used in which a detailed cross-section of tissue structure is imaged using the nonlinearity of the ultrasonic propagation speed in biological tissues.

The tissue harmonic imaging is a technique of imaging the cross-section of biological tissues using only the second harmonic of the harmonic component in echo signals from biological tissues, and features clear high-contrast imaging with reduced artifacts.

This has made an improvement in the image quality of diagnostic images in the present diagnostic ultrasonography, thus improving the performance of diagnostic ultrasonography.

A known method for extracting only a harmonic component is pulse inversion (PI) imaging (for example, Abiru Iwao, and Kamakura Tomoo, Cyouonpa parusu no hisenkeidenpan [Unlinear Propagation of Ultrasonic Pulse], Singakugihou, US 89-23, p. 53). In this pulse inversion imaging, two kinds of ultrasonic waves with inverted phases are sent to multiple scanning lines, and two echo signals corresponding to the two ultrasonic waves are received. Then only harmonic components are extracted from the biological tissues by adding the echo signals and removing fundamental components.

In the tissue harmonic imaging, only difference tones of the harmonic components contained in the echo signals from biological tissues are used to image the cross-section of the biological tissues (for example, refer to JP-A-2004-298620).

Although it is not a technique of imaging the cross-section of the biological tissues, a technique of imaging the dynamic behavior of blood has also been used by using the fact that contrast medium bubbles are extremely delicate.

A known method for extracting only echo components from contrast medium bubbles includes rate subtraction (RS) imaging (for example, refer to JP-A-8-336527). In this rate subtraction imaging, the same ultrasonic wave is sent to multiple scanning lines at high sound pressure two times and two echo signals corresponding to the two times of transmission are received. Then the two echo signals are differentiated to remove duplicate components, so that an echo component from the disappeared and deformed contrast medium bubbles is extracted.

In other words, since the contrast medium bubbles for use in diagnostic ultrasonography are very delicate, when ultrasonic waves are applied, most of the bubbles are broken instantly. Accordingly, the echo signal obtained by the second ultrasonic transmission becomes smaller than that by the first transmission. However, the echo signal from the biological tissue does not change significantly. Accordingly, the differential signal obtained by the two echo signals reflects the echo signal from the disappeared and deformed contrast medium bubbles. Thus, the use of the rate subtraction imaging removes the echo signal from the biological tissues to enable imaging of only the dynamic behavior of blood.

However, the tissue harmonic imaging has the problem of insufficient sensitivity at the depths of ultrasonic images in comparison with the technique of imaging the cross-section of biological tissues from the fundamental in echo signals.

BRIEF SUMMARY OF THE INVENTION

The present invention has been made in view of the above-described circumstances. Accordingly, it is an object of the invention to provide an ultrasonic diagnostic scanner and a method for processing ultrasonic signals capable of generating ultrasonic images with less artifacts and with sufficient sensitivity at the depths.

According to an aspect of the invention, there is provided an ultrasonic diagnostic scanner comprising: a transmitting and receiving unit that transmits two kinds of ultrasonic waves with inverted phases to each of a plurality of scanning lines and receives first and second echo signals corresponding to the two kinds of ultrasonic waves from one scanning line to another; a nonlinear-signal obtaining unit that obtains a nonlinear signal by adding up the first and second echo signals received by the transmitting and receiving unit; a fundamental-signal obtaining unit that obtains a fundamental signal including the first and second echo signals received by the transmitting and receiving unit; a composite-signal generating unit that generates a composite signal from the nonlinear signal and the fundamental signal; and an image display unit that displays an image based on the composite signal.

According to another aspect of the invention, there is provided an ultrasonic diagnostic scanner comprising: a transmitting and receiving unit that transmits and receives an ultrasonic wave containing a first frequency component and a second frequency component higher than the first frequency component to each of a plurality of scanning lines; a nonlinear-signal obtaining unit that obtains a nonlinear signal containing a difference-tone component of the first and second frequency components on the basis of the transmission and reception of the ultrasonic waves; a fundamental-signal obtaining unit that obtains a fundamental signal containing the first and second frequency components on the basis of the transmission and reception of the ultrasonic waves; a composite-signal generating unit that generates a composite signal from the nonlinear signal and the fundamental signal; and a display unit that displays an image based on the composite signal.

According to yet another aspect of the invention, there is provided an ultrasonic diagnostic scanner comprising: a transmitting and receiving unit that transmits two kinds of ultrasonic waves with inverted phases to each of a plurality of scanning lines and receives first and second echo signals corresponding to the two kinds of ultrasonic waves from one scanning line to another; a nonlinear-signal obtaining unit that obtains a nonlinear signal by adding up the first and second echo signals received by the transmitting and receiving unit; a fundamental-signal obtaining unit that obtains a fundamental signal by performing subtraction of the first and second echo signals received by the transmitting and receiving unit; a composite-signal generating unit that generates a composite signal from the nonlinear signal and the fundamental signal; and an image display unit that displays an image based on the composite signal.

According to yet another aspect of the invention, there is provided an ultrasonic diagnostic scanner comprising: a transmitting and receiving unit that transmits two kinds of ultrasonic waves with inverted phases, the ultrasonic waves each containing a first frequency component and a second frequency component higher than the first frequency component, to each of a plurality of scanning lines and receives first and second echo signals corresponding to the two kinds of ultrasonic waves from one scanning line to another; a nonlinear-signal obtaining unit that obtains a nonlinear signal containing a difference-tone component of the first and second frequency components on the basis of the transmission and reception of the ultrasonic waves; a fundamental-signal obtaining unit that obtains a fundamental signal by performing subtraction of the first and second echo signals received by the transmitting and receiving unit; a composite-signal generating unit that generates a composite signal from the nonlinear signal and the fundamental signal; and a display unit that displays an image based on the composite signal.

According to yet another aspect of the invention, there is provided a method for processing an ultrasonic signal, the method comprising: obtaining a nonlinear signal by transmitting two kinds of ultrasonic waves with inverted phases to each of a plurality of scanning lines and adding up first and second echo signals obtained by receiving reflected waves corresponding to the two kinds of ultrasonic waves from one scanning line to another; obtaining a fundamental signal including the first echo signal or the second echo signal; generating a composite signal from the nonlinear signal and the fundamental signal; and displaying an image based on the composite signal.

According to yet another aspect of the invention, there is provided a method for processing an ultrasonic signal, the method comprising: obtaining a nonlinear signal containing a difference-tone component of the first and second frequency components from an echo signal obtained by transmitting and receiving an ultrasonic waves containing a first frequency component and a second frequency component higher than the first frequency component for each of a plurality of scanning lines; obtaining a fundamental signal containing the first and second frequency components; generating a composite signal from the nonlinear signal and the fundamental signal; and displaying an image based on the composite signal.

According to yet another aspect of the invention, there is provided a method for processing an ultrasonic signal, the method comprising: obtaining a nonlinear signal by adding up first and second echo signals obtained by transmitting two kinds of ultrasonic waves with inverted phases to each of a plurality of scanning lines and receiving reflected waves corresponding to the two kinds of ultrasonic waves from one scanning line to another; obtaining a fundamental signal by performing subtraction of the first and second echo signals; generating a composite signal from the nonlinear signal and the fundamental signal; and displaying an image based on the composite signal.

According to yet another aspect of the invention, there is provided a method for processing an ultrasonic signal, the method comprising: obtaining a nonlinear signal containing a difference-tone component of the first and second frequency components from first and second echo signals obtained by transmitting two kinds of ultrasonic waves with inverted phases, the ultrasonic waves each containing a first frequency component and a second frequency component higher than the first frequency component, to each of a plurality of scanning lines and receiving reflected waves corresponding to the two kinds of ultrasonic waves from one scanning line to another; obtaining a fundamental signal by performing subtraction of the first and second echo signals; generating a composite signal from the nonlinear signal and the fundamental signal; and displaying an image based on the composite signal.

BRIEF DESCRIPTION OF THE SEVERAL VIEWS OF THE DRAWING

FIG. 16 is a flowchart for a diagnostic-image generation process in a case where the weighting-factor setting sequence according to a seventh embodiment is in operation; and FIG. 17 is a table showing the concept of an eighth embodiment of the invention.

DETAILED DESCRIPTION OF THE INVENTION

First to fifth embodiments of the invention will be described in detail with reference to the drawings.

First Embodiment

Figure 1:
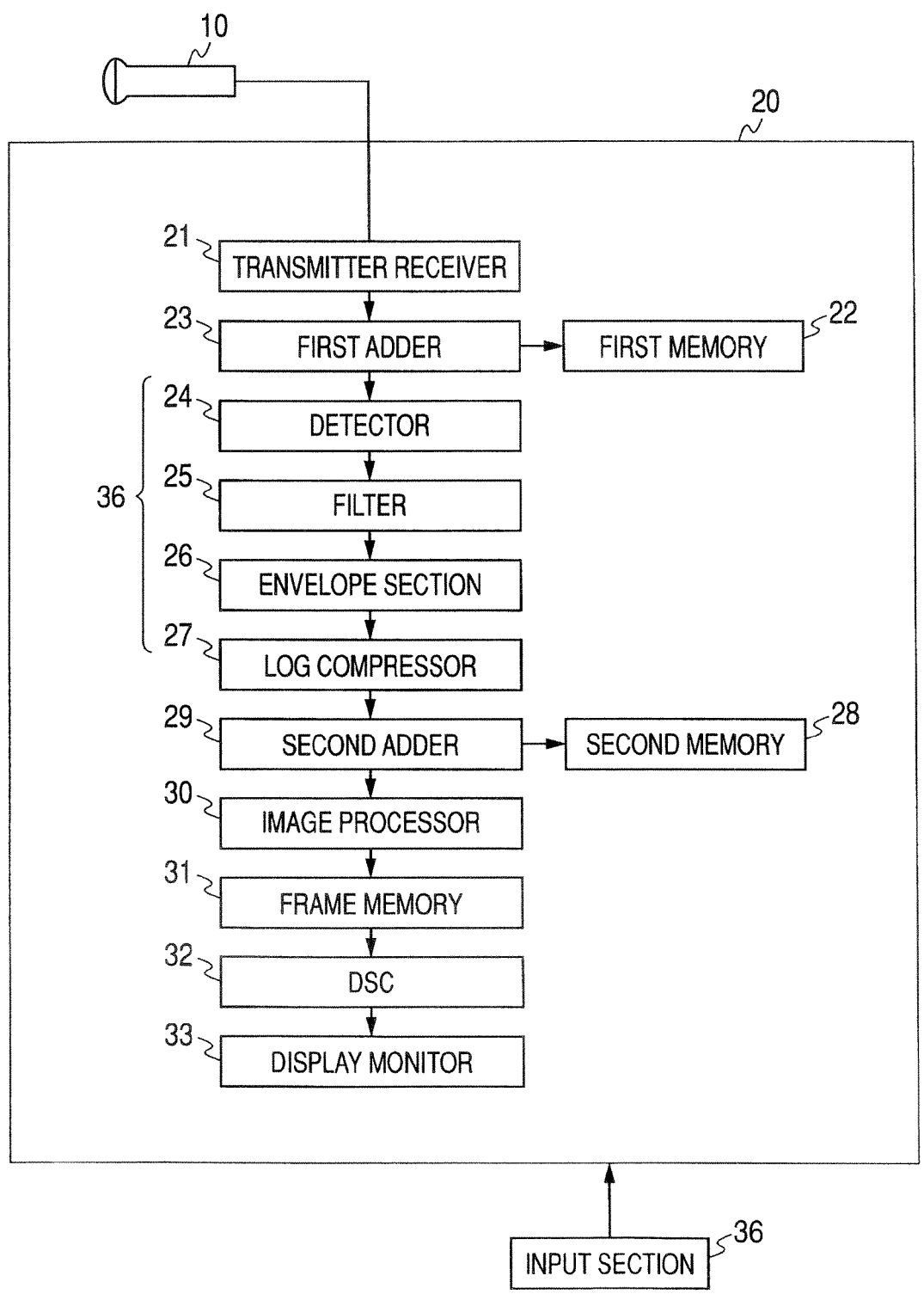
FIG. 1 is a block diagram of an ultrasonic diagnostic scanner according to a first embodiment of the invention.
Figure 2:
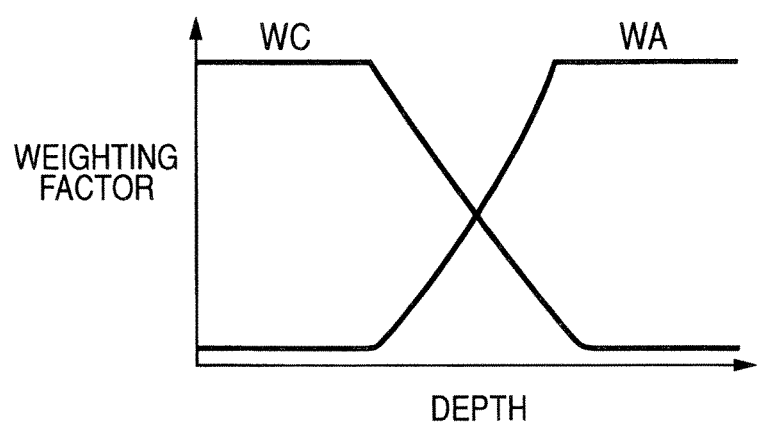
FIG. 2 is a graph of weighting factors according to the first embodiment.

Referring to FIGS. 1 and 2, a first embodiment of the invention will be described.

FIG. 1 is a block diagram of an ultrasonic diagnostic scanner according to the first embodiment.

As shown in FIG. 1, the ultrasonic diagnostic scanner includes an ultrasonic probe 10 and a main body 20.

The ultrasonic probe 10 is brought into contact with the surface of the body of a subject for sending and receiving ultrasonic waves, and has piezoelectric vibrators made of piezoelectric ceramics at the end. The piezoelectric vibrators are arranged in parallel at specified intervals, each of which serves as a channel.

The main body 20 includes a transmitter receiver (transmitting and receiving unit) 21, a first memory 22, a first adder 23, a detector 24, a filter 25, an envelope section 26, a log compressor 27, a second memory 28, a second adder (second signal processing unit) 29, an image processor (image generating unit) 30, a frame memory 31, a digital scan converter (hereinafter, referred to as a DSC) 32, and a display monitor (image display unit) 33.

The transmitter receiver 21 includes a transmitting section for transmitting ultrasonic waves and a receiving section for receiving echo signals from biological tissues. The echo signals from the biological tissues are received by the transmitter receiver 21 through the ultrasonic probe 10.

The first memory 22 stores an echo signal received by the transmitter receiver 21. When an echo signal is input from the transmitter receiver 21, the first adder 23 adds the echo signal to another echo signal stored in the first memory 22. When no echo signal is stored in the first memory 22, the echo signal from the transmitter receiver 21 passes through the first adder 23.

The detector 24 demodulates the echo signal from the first adder 23 with a frequency for the echo signal. The filter 25 filters the echo signal from the detector 24 according to the demodulation process to remove unnecessary components such as noise.

The envelope section 26 detects the envelope of the echo signal from the filter 25 to generate an envelope signal. The log compressor 27 log-compresses the envelope signal from the envelope section 26 to generate a processed signal.

In other words, the detector 24, the filter 25, the envelope section 26, and the log compressor 27 constitute a signal converting section (first signal processing section) 36 for processing the echo signal from the first adder 23 to generate a processed signal for use in imaging.

The second memory 28 stores the output of the first signal processing section, or the processed signal from the log compressor 27. The second adder 29 multiplies weighting factors to the processed signal stored in the second memory 28 and the processed signal from the log compressor 27, respectively, and adds them. The weighting factors are predetermined according to the depth of the subject, as will be described later, and are stored in a storage section (not shown) of the ultrasonic diagnostic scanner.

The image processor 30 provides various image processings to the processed signal from the second adder 29 to generate image frames. The frame memory 31 stores the image frames from the image processor 30 one by one.

The DSC 32 converts the scanning-signal train obtained by scanning to a scanning signal train in a general video format typified by television. The display monitor 33 displays the image data from the DSC 32 as an ultrasonic image.

Generation of Image by Ultrasonic Diagnostic Scanner

In the ultrasonic scanning according to the embodiment, two ultrasonic waves with the phases inverted 180 degrees, that is, first and second ultrasonic waves, are continuously transmitted every scanning line. The first and second ultrasonic waves are reflected by the surface of discontinuity of the acoustic impedance in the subject into two echo signals with the phases inverted 180 degrees, that is, first and second echo signals EA and EB corresponding to the first and second ultrasonic waves and received by the transmitter receiver 21. Although the first and second echo signals EA and EB contain both the fundamental and harmonic components, the harmonic component is extremely smaller than the fundamental component, so that they are assumed to be echo signals which reflect the fundamental component.

The first echo signal EA received first is stored in the first memory 22, and sent to the detector 24 through the first adder 23. When the second echo signal EB received later reaches the first adder 23, the first echo signal EA stored in the first memory 22 and the second echo signal EB are added up to generate a third echo signal EC.

The first and second echo signals EA and EB are inverted in phase by 180 degrees, as described above. Accordingly, when the first and second echo signals EA and EB are added up, the fundamental components in the first and second echo signals EA and EB are offset, so that only the harmonic components are enhanced double. This makes the third echo signal EC an echo signal that reflects the harmonic component from the biological tissues.

When the third echo signal EC is generated, the first echo signal EA has already advanced through the first adder 23. The preceding first echo signal EA and the third echo signal EC following the first echo signal EA are subjected to the demodulation by the detector 24, the filtering by the filter 25, the envelope detection by the envelope section 26, and the log-compression by the log compressor 27 into a first processed signal SA and a second processed signal SC, respectively. Since the first and second processed signals SA and SC are generated from the first and third echo signals EA and EC, they reflect the fundamental component and the harmonic component, respectively.

The first processed signal SA output from the log compressor 27 is temporarily stored in the second memory 28. When the second processed signal SC that is later output from the log compressor 27 reaches the second adder 29, the first processed signal SA stored in the second memory 28 is multiplied by a weighting factor WA, and the second processed signal SC reached to the second adder 29 is multiplied by a weighting factor WC, which are then added. Thus, a third processed signal SD composed of the first processed signal SA and the second processed signal SC is generated.

The third processed signal SD is expressed using the first processed signal SA and the second processed signal SC as follows:

$$SD = SA \times WA + SC \times WC.$$

Where the weighting factors WA and WC are determined in advance, which are stored in a storage section (not shown) of the ultrasonic diagnostic scanner.

The first processed signal SA reflects the fundamental component, while the second processed signal SC reflects the harmonic component. Accordingly, the third processed signal SD contains both the fundamental component and the harmonic component.

The contribution of the fundamental component and the harmonic component of the third processed signal SD depends on the relationship between the weighting factors WA and WC in terms of size. For example, when the weighting factor WA is large and the weighting factor WC is small, the third processed signal SD reflects the fundamental component more. In contrast, when the weighting factor WA is small and the weighting factor WC is large, the third processed signal SD reflects the harmonic component more.

FIG. 2 is a graph of the weighting factors WA and WC according to the first embodiment.

As shown in FIG. 2, the weighting factor WA is smaller at shallow depths and larger at deep depths. In contrast, the weighting factor WC is larger at shallow depths and smaller at deep depths. The weighting factors WA and WC are close to each other at the middle. Accordingly, the third processed signal SD reflects the harmonic component more at shallow depths, and reflects the fundamental component more at deep depths.

The third processed signal SD is subjected to various image processings by the image processor 30 into image frames, and then stored in the frame memory 31 one by one. The image frames accumulated in the frame memory 31 are scan-converted by the DSC 32 and displayed on the display monitor 33 as ultrasonic images one after another. The internal structure of the subject can also be displayed on the display monitor 33 as moving images. The operator such as a doctor makes a diagnosis while viewing the ultrasonic images.

Operation of the Embodiment

The third processed signal SD of the embodiment is generated by multiplying the first processed signal SA which reflects the fundamental component by the weighting factor WA, multiplying the second processed signal SC which reflects the harmonic component by the weighting factor WC, and adding them. The weighting factor WA for the first processed signal SA is set large at the shallow depths of the subject and smaller at the deep depths, while the weighting factor WC of the second processed signal SC is set smaller at the shallow depths of the subject and larger at the deep depths.

Accordingly, the ultrasonic images generated on the basis of the third processed signal SD reflects the harmonic component more at the shallow depths of the subject and reflects the fundamental component more at the deep depths. That is, the deep depths of the subject are imaged on the basis of the fundamental component. This prevents insufficient sensitivity of ultrasonic images even at the deep depths of the subject, thus providing the entire image with sufficient sensitivity for a diagnosis.

Since the shallow depths of the subject are imaged on the basis of the harmonic component, the occurrence of artifacts is remarkably prevented in comparison with imaging using only the fundamental component.

Thus, the embodiment can provide ultrasonic images with less artifacts and sufficient sensitivity even at the deep depths.

In this embodiment, the frequency bands of the first and second ultrasonic waves are not mentioned. The first and second ultrasonic waves sometimes have first and second frequency components, respectively. This results in that the third echo signal EC contains the difference-tone component of the first and second frequency components. Accordingly, for example, the third echo signal EC is filtered to extract only the difference-tone component. Then the second processed signal SC is generated on the basis of the extracted difference tone component. It is needless to say that the difference-tone component is one of harmonic components.

Even if the second processed signal SC is generated on the basis of the difference-tone component, the first and second processed signals SA and SC reflect the fundamental component and the harmonic component, respectively. Accordingly, when the first and second processed signals SA and SC are multiplied by the weighting factors, respectively, a high-quality ultrasonic image can be provided as in the above.

Second Embodiment

Figure 3:
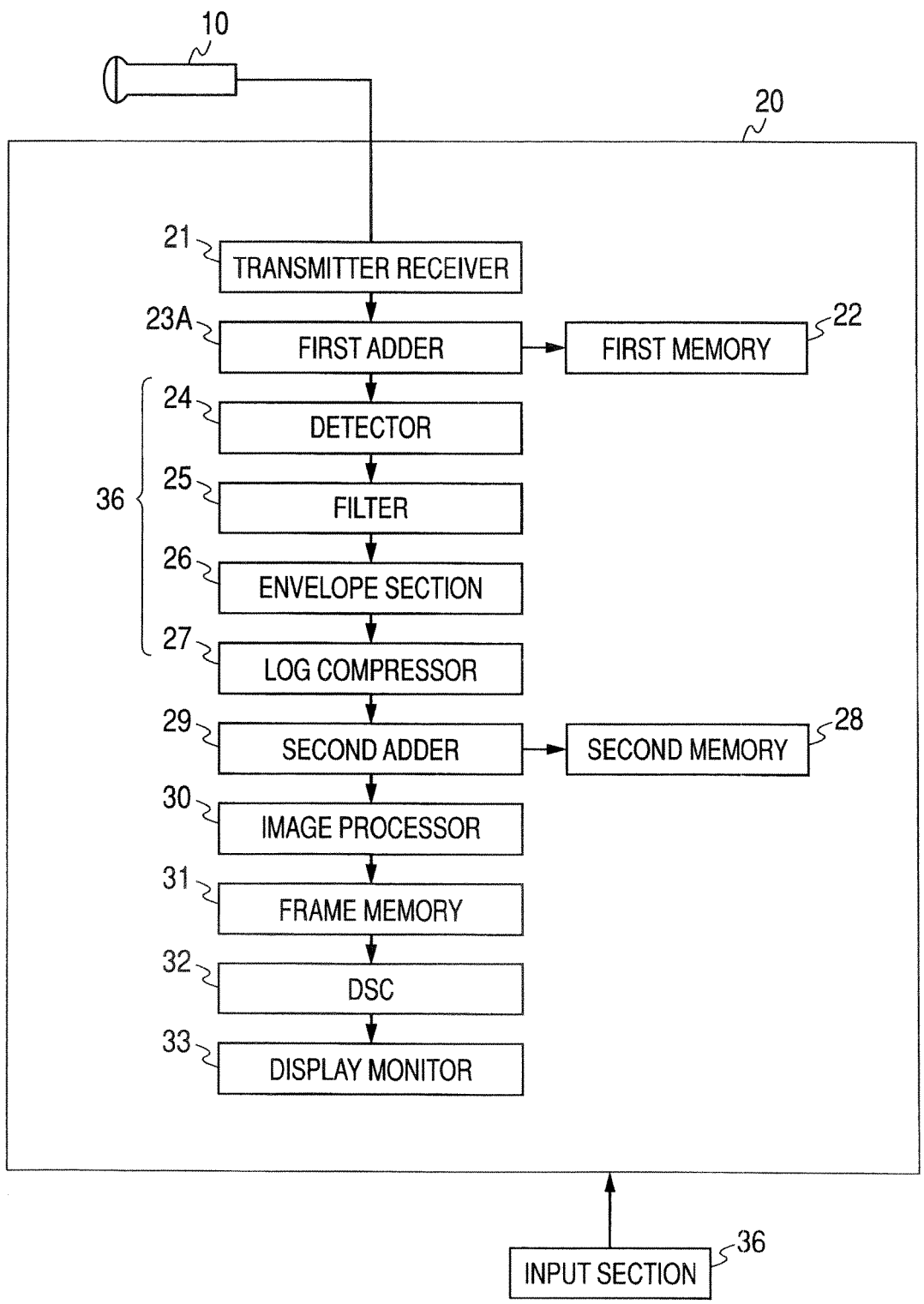
FIG. 3 is a block diagram of an ultrasonic diagnostic scanner according to a second embodiment of the invention.
Figure 4:
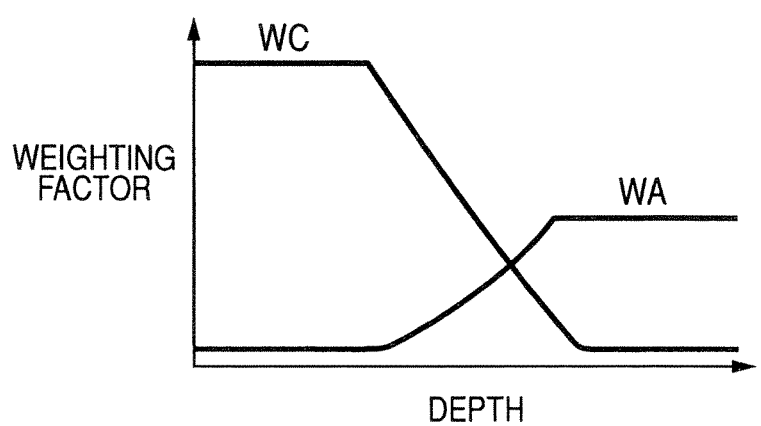
FIG. 4 is a graph of weighting factors according to the second embodiment.

Referring to FIGS. 3 and 4, a second embodiment of the invention will be described. The description of the same structure and operation as those of the first embodiment will be omitted.

FIG. 3 is a block diagram of an ultrasonic diagnostic scanner according to a second embodiment.

As shown in FIG. 3, this embodiment uses an adder-subtracter 23A (an adding unit and a subtracting unit) in place of the first adder 23 of the first embodiment.

The adder-subtracter 23A has the function of obtaining the difference between an echo signal, when input from the transmitter receiver 21, and another echo signal stored in the first memory 22. The subtraction is to obtain the value of the difference between the echo signals.

Generation of Image by Ultrasonic Diagnostic Scanner

In the ultrasonic scanning according to the second embodiment, two ultrasonic waves with the phases inverted 180 degrees, that is, first and second ultrasonic waves, are continuously transmitted every scanning line. The first and second ultrasonic waves are reflected by the surface of discontinuity of the acoustic impedance in the subject into two echo signals with the phases inverted 180 degrees, that is, first and second echo signals EA and EB corresponding to the first and second ultrasonic waves and received by the transmitter receiver 21.

The first echo signal EA received first is temporarily stored in the first memory 22. When the second echo signal EB received later reaches the adder-subtracter 23A, the first echo signal EA stored in the first memory 22 and the second echo signal EB are added up to generate a third echo signal EC. Subsequently, the first echo signal EA stored in the first memory 22 and the second echo signal EB received later are subjected to subtraction to generate a fourth echo signal EC'.

The first and second echo signals EA and EB are inverted in phase by 180 degrees, as described above. Accordingly, when the first and second echo signals EA and EB are added up, the fundamental components in the first and second echo signals EA and EB are offset, so that only the harmonic components are enhanced double. Thus, the third echo signal EC becomes an echo signal that reflects the harmonic component from the biological tissues. In contrast, when the first and second echo signals EA and EB are subjected to subtraction, the harmonic components in the first and second echo signals EA and EB are offset, so that only the fundamental components are enhanced double, so that the fourth echo signal EC' becomes an echo signal that reflects the fundamental component from the biological tissues.

When the fourth echo signal EC' is generated, the third echo signal EC has already advanced through the adder-subtracter 23A. The preceding third echo signal EC and the fourth echo signal EC' are subjected to the demodulation by the detector 24, the filtering by the filter 25, the envelope detection by the envelope section 26, and the log-compression by the log compressor 27 into a first processed signal SC and a second processed signal SC', respectively. Since the first and second processed signals SC and SC' are generated from the third and fourth echo signals EC and EC', they reflect the harmonic component and the fundamental component, respectively.

The first processed signal SC output from the log compressor 27 is temporarily stored in the second memory 28. When the second processed signal SC' that is later output from the log compressor 27 reaches the second adder 29, the first processed signal SC stored in the second memory 28 is multiplied by a weighting factor WC, and the second processed signal SC' that has reached the second adder 29 is multiplied by a weighting factor WC', which are then added. Thus, a third processed signal SD composed of the first processed signal SC and the second processed signal SC' is generated.

The third processed signal SD is expressed using the first processed signal SC and the second processed signal SC' as follows:

$$SD=SC \times WC + SC' \times WC'.$$

Where the weighting factors WC and WC' are determined in advance, and are stored in a storage section (not shown) of the ultrasonic diagnostic scanner.

The first processed signal SC reflects the harmonic component, and the second processed signal SC' reflects the fundamental component. Accordingly, the third processed signal SD contains both the harmonic component and the fundamental component.

The contribution of the harmonic component and the fundamental component of the third processed signal SD depends on the relationship between the weighting factors WC and WC' in terms of size. For example, when the weighting factor WC is large and the weighting factor WC' is small, the third processed signal SD reflects the harmonic component more. In contrast, when the weighting factor WC is small and the weighting factor WC' is large, the third processed signal SD reflects the fundamental component more.

FIG. 4 is a graph of the weighting factors WC and WC' according to the second embodiment.

As shown in FIG. 4, the weighting factor WC is larger at shallow depths and smaller at deep depths. In contrast, the weighting factor WC' is smaller at shallow depths and larger at deep depths. The weighting factors WC and WC' are close to each other at the middle. Accordingly, the third processed signal SD reflects the harmonic component at shallow depths, and reflects the fundamental component at deep depths. The curve of the weighting factor WC' that expresses the contribution of the fundamental component is gentler than the curve of the weighting factor WA of the first embodiment.

The third processed signal SD is subjected to various image processings by the image processor 30 into image frames, and then stored in the frame memory 31 one by one. The image frames accumulated in the frame memory 31 are scan-converted by the DSC 32 and displayed on the display monitor 33 as ultrasonic images one after another. The internal structure of the subject can also be displayed on the display monitor 33 as moving images. The operator such as a doctor makes a diagnosis while viewing the ultrasonic images.

Operation of the Embodiment

The second processed signal SC' of this embodiment is a signal which mainly reflects the fundamental component as is the first processed signal SA of the first embodiment. However, the second processed signal SC' is generated from a fourth echo signal EC' in which the fundamental component is enhanced double, so that it has the strength about two times as high as that of the first processed signal SA of the first embodiment.

Therefore, the scale of the weighting factor WC' that expresses the contribution of the fundamental component is reduced to about one half. Accordingly, even if the depths of the biological tissues cannot be sufficiently light even if the weighting factor WA is set to the maximum in the first embodiment, the second embodiment can sufficiently cope with it.

In this embodiment also, the frequency bands of the first and second ultrasonic waves are not mentioned. The first and second ultrasonic waves sometimes have first and second frequency components, respectively. In this case, the third echo signal EC is filtered to extract only a difference-tone component therefrom, as in the first embodiment. Then, the second processed signal SC is generated from the extracted difference-tone component.

Even if the second processed signal SC is generated on the basis of the difference-tone component, the first and second processed signals SC and SC' reflect the fundamental component and the harmonic component, respectively. Accordingly, when the first and second processed signals SC and SC' are multiplied by the weighting factors, respectively, a high-quality ultrasonic image can be provided as in the above.

Third Embodiment

Figure 5:
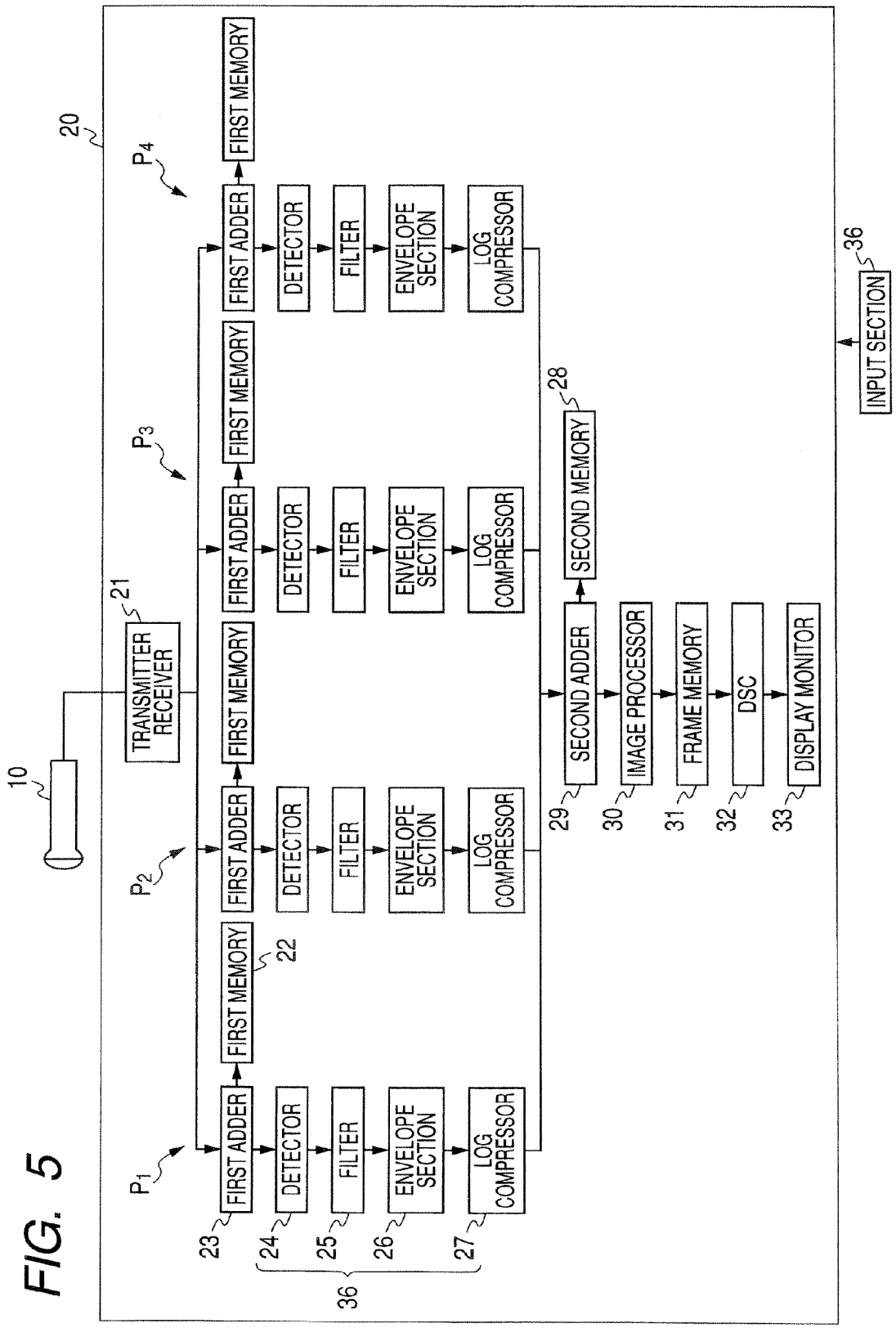
FIG. 5 is a block diagram of an ultrasonic diagnostic scanner according to a third embodiment of the invention.

Referring to FIG. 5, a third embodiment of the invention will be described. The description of the same structure and operation as those of the first and second embodiments will be omitted.

FIG. 5 is a block diagram of an ultrasonic diagnostic scanner according to a third embodiment.

As shown in FIG. 5, this embodiment applies a frequency compound to the ultrasonic diagnostic scanner according to the first embodiment. Accordingly, in the ultrasonic diagnostic scanner of this embodiment, the down stream of the transmitter receiver 21 is divided into four paths P1 to P4, which are joined at the up stream of the second adder 29 again.

The structure of the paths P1 to P4, that is, the structure between the transmitter receiver 21 and the second adder 29 is almost the same as that of the first embodiment. Only the frequencies of the detector 24 and the filter 25 are different.

Specifically, the detectors 24 of the paths P1 to P4 of this embodiment demodulate the first and second echo signals EA and EB that the transmitter receiver 21 has received at different frequencies, 1 MHz, 2 MHz, 3 MHz, and 4 MHz, respectively. The filters 25 of the paths P1 to P4 filter with frequencies according to the demodulation, respectively.

Generation of Image by Ultrasonic Diagnostic Scanner

The first and second echo signals EA and EB received by the transmitter receiver 21 are each divided into the paths P1 to P4, and processed path to path. For example, first and second echo signals EA1 and EB1 sent to the path P1 are processed as in the first embodiment into a first processed signal SA1 that reflects the fundamental component and a second processed signal SC1 that reflects the harmonic component SC1, and are output from the log compressor 27 one by one. The first and second signals SA1 and SC1 correspond to the first and second processed signals SA and SC of the first embodiment.

Since the foregoing process is executed for the paths P1 to P4, eight kinds of signals, that is, the first processed signals SA1 to SA4 and the second processed signals SC1 to SC4 are generated. The first processed signals SA1 to SA4 are signals that reflect the fundamental component, while the second processed signals SC1 to SC4 are signals that reflect the harmonic component.

As described above, the frequencies of the detector 24 and the filter 25 are different from path to path. Accordingly, the first signals SA1 to SA4 are different in frequency and the second signals SC1 to SC4 are also different in frequency.

The first processed signals SA1 to SA4 output from the respective log compressors 27 of the paths P1 to P4 are temporarily stored in the second memory 28. When the second processed signals SC1 to SC4 that are later output from the log compressors 27 reach the second adder 29, the first processed signals SA1 to SA4 stored in the second memory 28 are multiplied by predetermined weighting factors WA1 to WA4, respectively, and the second processed signals SC1 to SC4 that have reached the second adder 29 are multiplied by weighting factors WB1 to WB4, all of which are then added. Thus, a third processed signal SD composed of the first processed signals SA1 to SA4 and the second processed signals SC1 to SC4 is generated.

The third processed signal SD is expressed using the first processed signals SA1 to SA4 and the second processed signals SC1 to SC4 as follows:

$$SD = SA1 \times WA1 + SA2 \times WA2 + SA3 \times WA3 + SA4 \times WA4 + SC1 \times WC1 + SC2 \times WC2 + SC3 \times WC3 + SC4 \times WC4.$$

The first processed signals SA1 to SA4 are signals that reflect the fundamental component, while the second processed signals SC1 to SC4 are signals that reflect the harmonic component. The frequencies of the first processed signals SA1 to SA4 are different and the frequencies of the second processed signals SC1 to SC4 are also different.

In other words, the third processing signal SD is composed of four kinds of fundamental component with different frequencies and four kinds of harmonic components with different frequencies.

The third processed signal SD is subjected to various image processings by the image processor 30 into image frames, and then stored in the frame memory 31 one by one. The image frames accumulated in the frame memory 31 are scan-converted by the DSC 32 and displayed on the display monitor 33 as ultrasonic images one after another. The operator such as a doctor makes a diagnosis while viewing the ultrasonic images.

Operation of the Embodiment

The third processed signal SD of this embodiment is composed of four kinds of fundamental components with different frequencies and four kinds of harmonic components with different frequencies. Accordingly, the ultrasonic images generated on the basis of the third processing signal SD become extremely dense without speckle owing to the effect of the compound. As a result, the details of the biological tissues can be imaged in the ultrasonic imaging, improving the performance of the diagnosis.

Although this embodiment applies a frequency compound to the ultrasonic diagnostic scanner of the first embodiment, the invention is not limited to that but the frequency compound may be applied to the ultrasonic diagnostic scanner according to the second embodiment.

Fourth Embodiment

Figure 6:
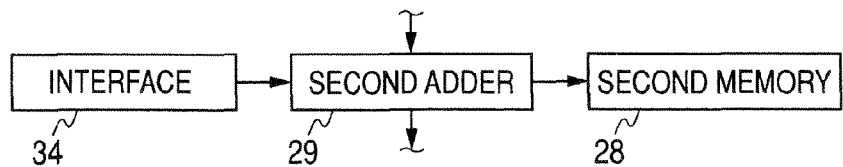
FIG. 6 is a block diagram of the periphery of an interface of an ultrasonic diagnostic scanner according to a fourth embodiment of the invention.
Figure 7:
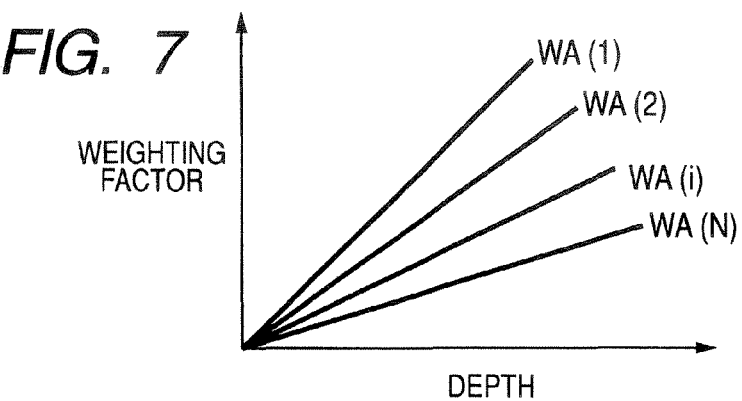
FIG. 7 is a graph of a weighting factor according to the fourth embodiment.

Referring to FIGS. 6 and 7, a fourth embodiment of the invention will be described. The description of the same structure and operation as those of the first to third embodiments will be omitted.

FIG. 6 is a block diagram of the periphery of an interface 34 of an ultrasonic diagnostic scanner according to the fourth embodiment. FIG. 7 is a graph of a weighting factor WC according to this embodiment.

As shown in FIG. 6, this embodiment includes an interface 3 (variable means) 34 added to the ultrasonic diagnostic scanner of the first embodiment. The interface 34 is for inputting a weighting factor designated by an operator such as a doctor. The weighting factor of this embodiment varies linearly with the depth. Examples of the interface 34 include a dial, sliding switch, button, and touch-panel switch.

The second adder 29 gives a weight with the weighting factor input from the interface 34 to generate a third processing signal SD for use in ultrasonic imaging. For example, assume that weighting factors WA and WC have the relation, WC=1−WA. Then, as shown in FIG. 7, the ratio of the fundamental component to the harmonic component in an ultrasonic image can be freely changed by adjusting only one weighting factor WA to switch the inclination thereof as shown in (1) to (N). Furthermore, this embodiment can cope with extremely slight changes in weighting factor with the form of the interface 34.

Accordingly, the ultrasonic diagnostic scanner of this embodiment allows the operator such as a doctor to obtain an optimum image for a diagnosis only by adjusting the interface 34 while viewing the ultrasonic images, thus improving the operability.

Although this embodiment is described for the case in which the interface 34 is added to the ultrasonic diagnostic scanner of the first embodiment, the invention is not limited to that. For example, the interface 34 may be added to that of the second or third embodiment. Particularly, the ultrasonic diagnostic scanner of the third embodiment which has eight weighting factors can generate various ultrasonic images by adjusting the factors.

Fifth Embodiment

Figure 8:
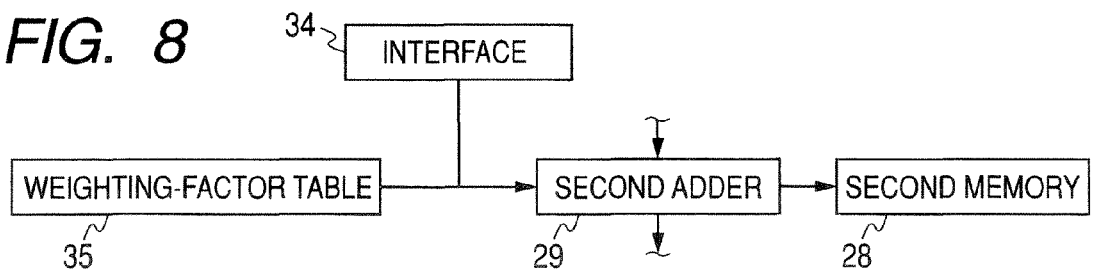
FIG. 8 is a block diagram of the periphery of a weighting-factor table of an ultrasonic diagnostic scanner according to a fifth embodiment of the invention.
Figure 9:
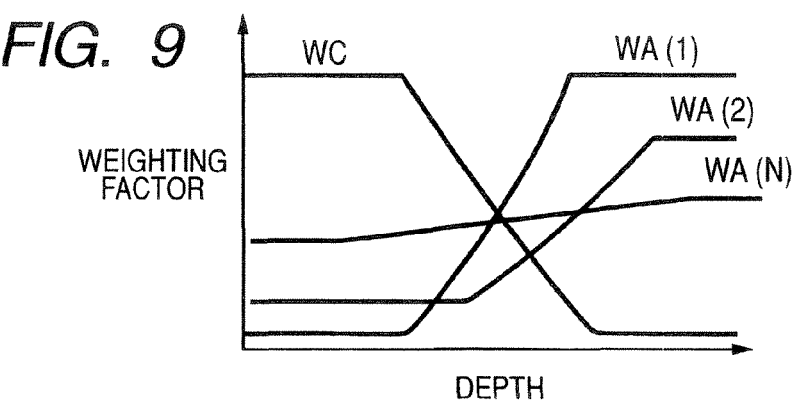
FIG. 9 is a graph of weighting factors according to the fifth embodiment.

Referring to FIGS. 8 and 9, a fifth embodiment of the invention will be described. The description of the same structure and operation as those of the first to fourth embodiments will be omitted.

FIG. 8 is a block diagram of the periphery of a weighting-factor table 35 of an ultrasonic diagnostic scanner according to the fifth embodiment. FIG. 9 is a graph of weighting factors WC and WA(1) to WA(n) according to this embodiment.

As shown in FIG. 8, this embodiment includes an interface 34A (variable means) and the weighting-factor table 35 added to the ultrasonic diagnostic scanner of the first embodiment. The interface 34A is for inputting various set information including the transmission frequency of the ultrasonic waves and weighting factors designated by an operator such as a doctor. The weighting-factor table 35 stores the weighting factor WC and the weighting factors WA(1) to WA(n)

corresponding to the transmission frequency of the ultrasonic wave, and the depth of display.

When set information, that is, the transmission frequency and the depth of display, is input from the interface 34A, a weighting factor WA(i) according to the set information is automatically selected from the weighting-factor table 35, and the weighting factors WC and WA(i) are input to the second adder 29. Then the second adder 29 assigns a weight with the weighting factors WC and WA(i) input from the weighting-factor table 35 to generate a third processing signal SD for use in ultrasonic imaging.

Accordingly, since an ultrasonic image according to the transmission frequency of the ultrasonic wave and the display depth input from the interface 34A is generated, the operator can freely change the transmission frequency without worrying about a decrease in sensitivity. This increases the variation of set conditions, thus improving diagnostic performance.

Moreover, an ultrasonic image corresponding to the set conditions is automatically generated only by inputting the set conditions from the interface 34A. This remarkably reduces the work load on the operator in comparison with that for the case in which all conditions must be set every diagnosis.

Although this embodiment is described for the case in which the interface 34A and the weighting-factor table 35 are added to the ultrasonic diagnostic scanner of the first embodiment, the invention is not limited to that. For example, the interface 34A and the weighting-factor table 35 may be added to that of the second or third embodiment.

Although the first to fifth embodiments have been described for a B-mode image, the invention may be applied to the generation of an ultrasonic image other than the B-mode image. For example, when the invention is applied to the generation of an M-mode image or a three-dimensional image, an M-mode image or a three-dimensional image with sufficient sensitivity at the depths of the subject can be provided by switching the display mode to the M mode or the three dimensional mode, allowing switching of the modes at a diagnosis.

Sixth Embodiment

Referring to FIGS. 10 to 15, a sixth embodiment of the invention will be described.

Figure 10:
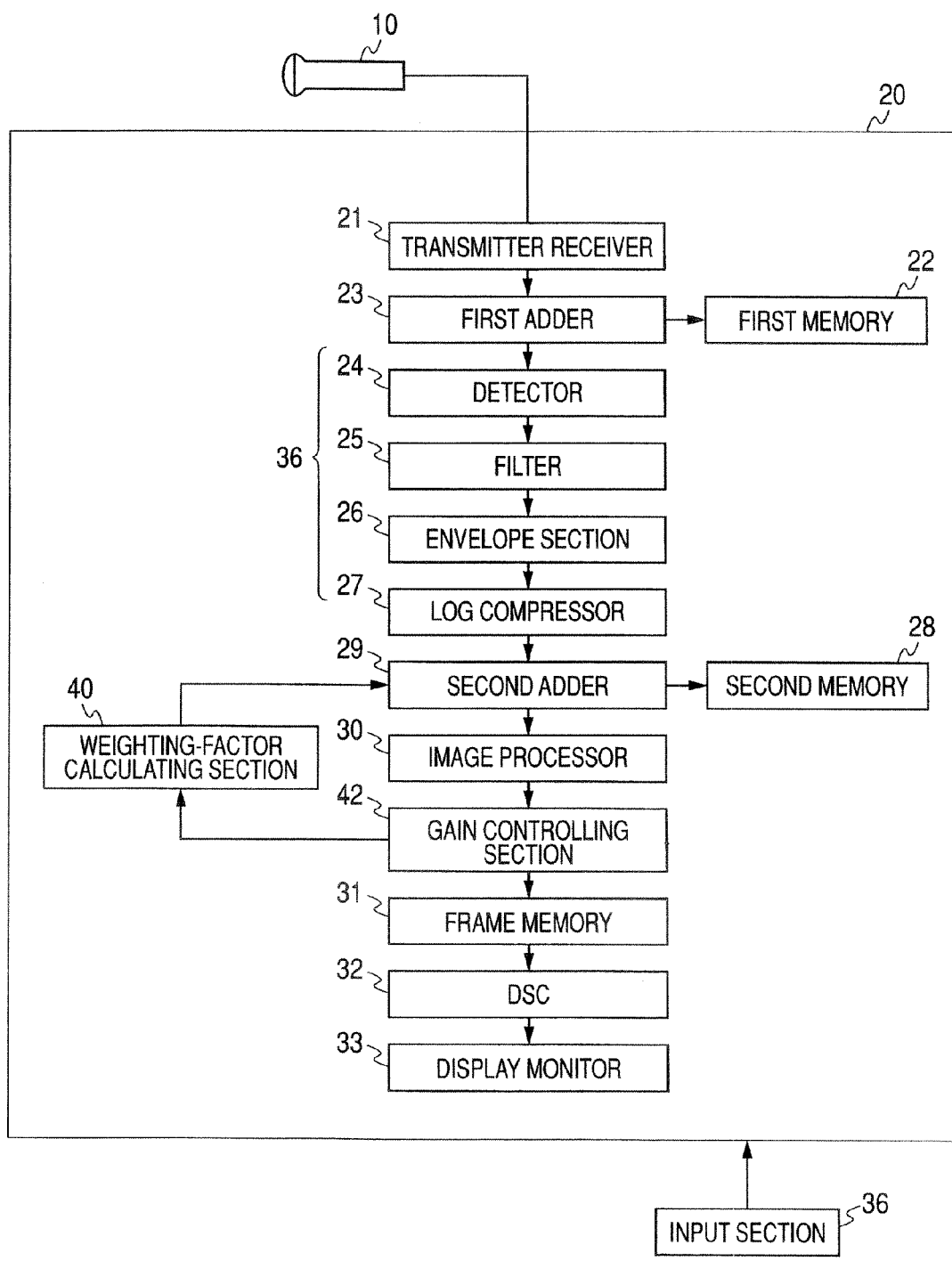
FIG. 10 is a block diagram of an ultrasonic diagnostic scanner according to a sixth embodiment of the invention.

FIG. 10 is a block diagram of an ultrasonic diagnostic scanner according to the sixth embodiment.

As shown in FIG. 10, the ultrasonic diagnostic scanner of this embodiment includes an ultrasonic probe 10 and a main body 20.

The ultrasonic probe 10 is detachably connected to the main body 20, and has a 2D-array vibrator at the end. This allows the ultrasonic probe 10 of the embodiment to execute three-dimensional transmission and reception of ultrasonic waves.

The main body 20 includes a transmitter receiver (transmitting and receiving unit) 21, a first memory 22, an adder (component extracting unit) 23, a detector 24, a filter 25, an envelope section 26, a log compressor 27, a second memory 28, a second adder (composite-signal generating unit) 29, an image processor 30, a gain controlling section (gain calculating unit) 42, a weighting-factor calculating section 40, a frame memory 31, a DSC 32, a monitor (display unit) 33, and an input section (instructing unit) 36.

The image processor 30 applies various image processings to the image signal from the second adder 29. The gain controlling section 42 controls the gain on the basis of the image signal from the image processor 30. The weighting-factor calculating section 40 calculates a weighting factor on the basis of the gain from the gain controlling section 42.

Generating Diagnostic Image

In the scanning sequence of this embodiment, two ultrasonic waves with inverted phases, that is, first and second ultrasonic waves, are continuously transmitted every scanning line. The first and second ultrasonic waves are reflected by the surface of discontinuity of the acoustic impedance in the subject into two echo signals with inverted phases, that is, first and second echo signals EA and EB corresponding to the first and second ultrasonic waves and received by the transmitter receiver 21.

Although the first and second echo signals EA and EB contain both a fundamental component and a harmonic component, the harmonic component is extremely smaller than the fundamental component, so that they are assumed to reflect the fundamental component.

The first echo signal (second component) EA received first is stored in the first memory 22, and sent to the detector 24 through the first adder 23. When the second echo signal EB received later reaches the first adder 23, the first echo signal EA stored in the first memory 22 and the second echo signal EB that has reached the first adder 23 are added up to generate a third echo signal (first component) EC.

The first and second echo signals EA and EB are inverted in phase, as described above. Accordingly, when the first and second echo signals EA and EB are added up, the fundamental components in the first and second echo signals EA and EB are offset, so that only the harmonic components are enhanced double. Thus, the third echo signal EC reflects the harmonic component from the biological tissues.

When the third echo signal EC is generated, the first echo signal EA has already advanced forward from the first adder 23. The preceding first echo signal EA and the third echo signal EC following the first echo signal EA are subjected to the demodulation by the detector 24, the filtering by the filter 25, the envelope detection by the envelope section 26, and the log compression by the log compressor 27 into a first image signal SA and a second image signal SC, respectively. Since the first and second image signals SA and SC are generated from the first and third echo signals EA and EC, respectively, they reflect the fundamental component and the harmonic component, respectively.

The first image signal SA output from the log compressor 27 is temporarily stored in the second memory 28. When the second image signal SC that is output later from the log compressor 27 reaches the second adder 29, the first image signal SA stored in the second memory 28 is multiplied by a weighting factor WA, and the second image signal SC that has reached the second adder 29 is multiplied by a weighting factor WC, which are then added. Thus, a third image signal SD composed of the first image signal SA and the second image signal SC is generated.

The third image signal SD is expressed using the first image signal SA and the second image signal SC as follows:

$$SD = SA \times WA + SC \times WC.$$

Where the weighting factors WA and WC are calculated by the weighting-factor calculating section 40. The method for calculating them will be described later.

The third image signal SD is subjected to various image processings by the image processor 30, and then stored in the frame memory 31 one by one. The third processing signals SD accumulated in the frame memory 31 are scan-converted by the DSC 32 and displayed on the display monitor 33 as ultrasonic images one after another. The display monitor 33 can display the internal structure of the subject as moving images according to the selection of the way of display.

The first image signal SA reflects the fundamental component, and the second image signal SC reflects the harmonic component, as described above. Accordingly, the third processing signal SD contains both the fundamental component and the harmonic component.

The contribution of the fundamental component and the harmonic component of the third image signal SD depends on the relationship between the weighting factors WA and WC in terms of size. For example, when the weighting factor WA is large and the weighting factor WC is small, the third image signal SD reflects the fundamental component more, that is, contains more fundamental component. In contrast, when the weighting factor WA is small and the weighting factor WC is large, the third image signal SD reflects the harmonic component more, that is, contains less fundamental component.

Figure 11:
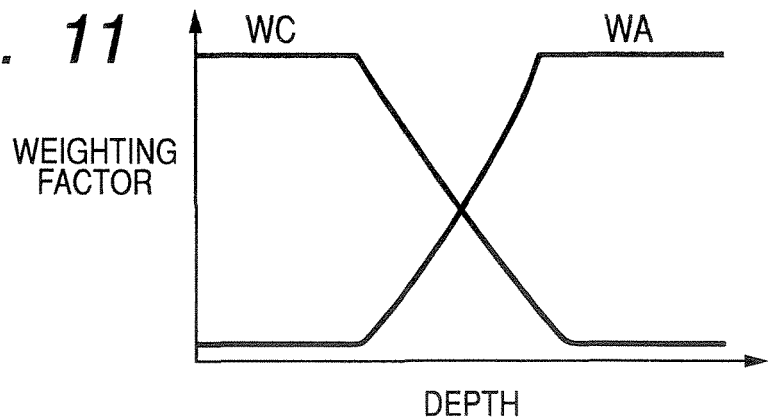
FIG. 11 is a graph of weighting factors according to the sixth embodiment.

FIG. 11 is a graph of the weighting factors WA and WC according to this embodiment.

As shown in FIG. 11, the weighting factor WA is smaller at shallow depths and larger at deep depths. In contrast, weighting factor WC is larger at shallow depths and smaller at deep depths. The weighting factors WA and WC are close to each other at the middle. Accordingly, the third image signal SD reflects the harmonic component at shallow depths, and reflects the fundamental component at deep depths.

Sequence of Setting Weighting Factors WA and WC

Figure 12:
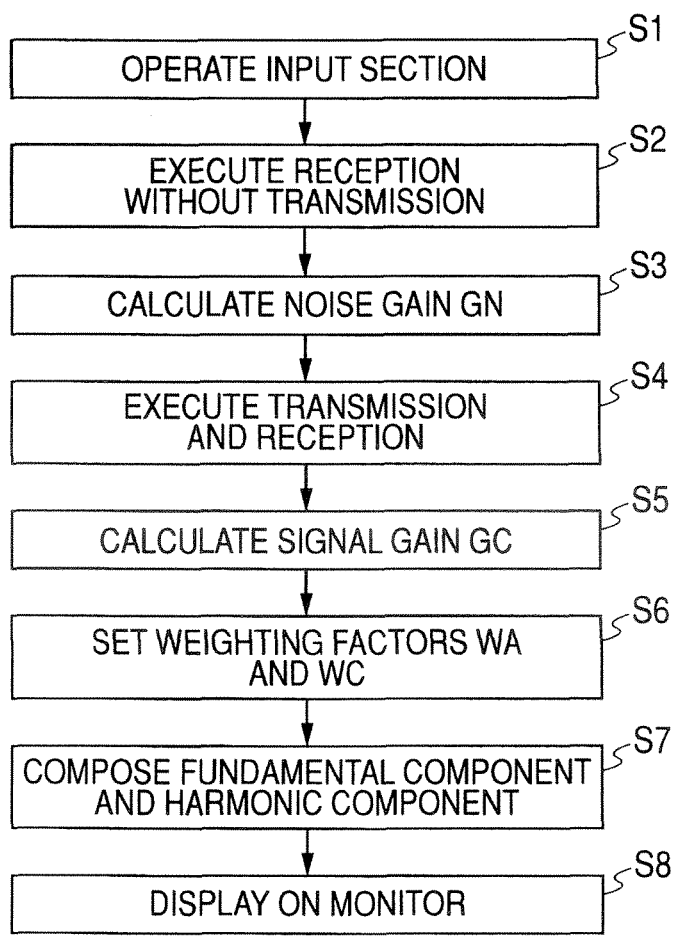
FIG. 12 is a flowchart for the process of generating diagnostic images while the weighting-factor setting sequence of the sixth embodiment is in operation.

FIG. 12 is a flowchart for the process of generating diagnostic images while the setting sequence for the weighting factors WA and WC of the embodiment is in operation.

As shown in FIG. 12, when the input section 36 is pushed (step S1), the setting sequence for the weighting factors WA and WC is started. In the setting sequence for the weighting factors WA and WC, the transmitter receiver 21 first performs reception of one frame without transmission (step S2). Here, reception without transmission is defined as performing reception only without performing transmission of an ultrasonic wave. Accordingly, when one frame of reception without transmission is executed by the transmitter receiver 21, a noise signal for one frame will be generated due to the internal noise inherent in the ultrasonic probe 10 or the main body 20. The noise signal from the ultrasonic probe 10 or the main body 20 is sometimes called a white noise because it is displayed in white on the image display 33.

The generated noise signal is processed as is the echo signal, and then sent to the gain controlling section 42, where a noise gain GN such that the strength of the noise signal becomes constant along the depth of the subject is calculated (step S3).

The transmitter receiver 21 then transmits and receives one frame to the subject (step S4). The transmission and reception is executed according to the above-described sequence. Accordingly, when the transmission and reception of one frame is executed by the transmitter receiver 21, one frame of the second image signal SC which reflects a harmonic component is generated.

The generated second image signal SC is sent to the gain controlling section 42, where a signal gain GC such that the strength of the second processing signal SC, that is, the strength of the harmonic component becomes constant along the depth of the subject is calculated (step S5).

The calculated noise gain GN and signal gain GC are sent to the weighting-factor calculating section 40, where the weighting factor WA for the first image signal SA and the weighting factor WC for the second image signal SC are calculated from the noise gain GN and the signal gain GC (step S6). Thus, the setting sequence for the weighting factors WA and WC is completed.

Upon completion of the setting sequence for the weighting factors WA and WC, the calculated weighting factors WA and WC are sent to the second adder 29, as described above, where they are multiplied by the first and second image signals SA and SC, respectively. Thus the third image signal SD composed of the fundamental component and the harmonic component is generated (step S7). The generated third image signal SD is displayed on the display monitor 33 one by one (step S8).

Figure 13:
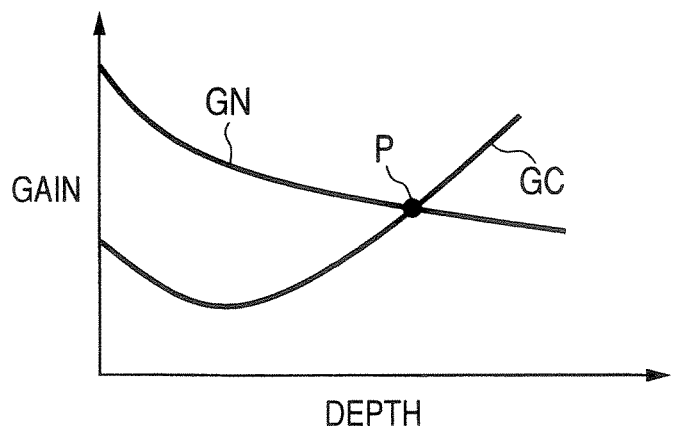
FIG. 13 is a graph of a noise gain and a signal gain of the sixth embodiment.

FIG. 13 is a graph of the noise gain GN and the signal gain GC of the embodiment.

As shown in FIG. 13, the noise gain GN and the signal gain GC intersect at a depth. The noise gain GN is lower than the signal gain GC at a region deeper than the intersecting point P. This shows that the strength of the noise signal in a region deeper than the intersecting point P is larger than that of the second image signal SC.

Accordingly, when the gain of the diagnostic image is set to the signal gain GC, the harmonic component is not clearly displayed in the region deeper than the intersecting point P because of the white noise. In contrast, in the region shallower than the intersecting point P, the harmonic component is clearly displayed without the disturbance of the white noise.

Accordingly, this embodiment uses the intersecting point P of the noise gain GN and the signal gain GC to set the weighting factors WA and WC. Specifically, the weighting factor WA is set high in the region deeper than the intersecting point P, while the weighting factor WA is set low in the region shallower than the intersecting point P. Thus, the proportion of the fundamental component is high in the region deeper than the intersecting point P, while it is low in the region shallower than the intersecting point P.

However, when the weighting factor WA increases rapidly from the intersecting point P, discontinuity is formed in the generated diagnostic image. Therefore, the proportion of the fundamental component is set so that the weighting factor WA changes gradually from the region shallower than the intersecting point P to the deeper region.

The proportion of the fundamental component of the embodiment is zero percent in the depths up to 60 percent of the intersecting point P, and increases linearly in the depths of 60 to 240 percent of the intersecting point P to reach 100 percent at the depths deeper than 240 percent of the intersecting point P. It has been shown that these proportions allow generation of high-quality diagnostic images from the shallow region to the deep region. The values of the proportion are just a few examples; other proportions are possible.

Experimental Results with Phantom

Figure 14A:
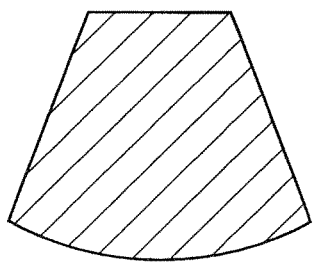
FIG. 14A is a diagram of a diagnostic phantom image with an attenuation of 0.7 [dB/MHz·cm] according to the sixth embodiment.
Figure 14B:
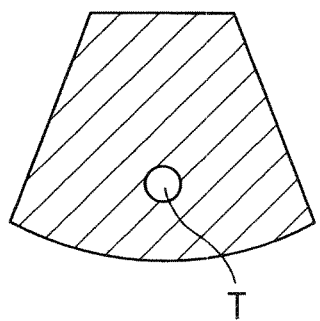
FIG. 14B is a diagram of a diagnostic phantom image with an attenuation of 0.7 [dB/MHz·cm] according to the sixth embodiment.

FIGS. 14A and 14B are diagnostic phantom images with an attenuation of 0.7 [dB/MHz·cm] in this embodiment. FIG. 14A shows a case in which the setting sequence for the weighting factors WA and WC is out of operation; FIG. 14B shows a case in which the setting sequence for the weighting factors WA and WC is in operation. The phantom has a spherical target T embedded in the depths.

As shown in FIG. 14A, when the setting sequence for the weighting factors WA and WC is out of operation, the target T is not drawn. This indicates that the sensitivity of the diagnostic image is low at the depths.

However, as shown in FIG. 14B when the setting sequence for the weighting factors WA and WC is in operation, the target T is drawn at the depths of the diagnostic image. This indicates that the sensitivity of the diagnostic image at the depths becomes high because the setting sequence for the weighting factors WA and WC is brought into operation.

Figure 15A:
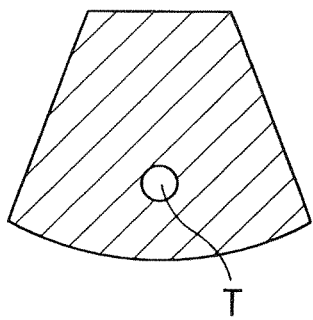
FIG. 15A is a diagram of a diagnostic phantom image with an attenuation of 0.3 [dB/MHz·cm] according to the sixth embodiment.
Figure 15B:
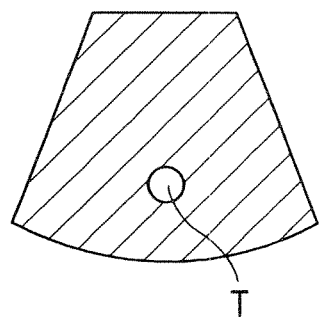
FIG. 15B is a diagram of a diagnostic phantom image with an attenuation of 0.3 [dB/MHz·cm] according to the sixth embodiment.

FIGS. 15A and 15B are diagnostic phantom images with an attenuation of 0.3 [dB/MHz·cm] in this embodiment. FIG. 15A shows a case in which the setting sequence for the weighting factors WA and WC is out of operation; FIG. 15B shows a case in which the setting sequence for the weighting factors WA and WC is in operation. The phantom has a spherical target T embedded in the depths.

As shown in FIG. 15A, when the setting sequence for the weighting factors WA and WC is out of operation, the target T is drawn at the depths of the diagnostic image. This indicates that the sensitivity of the diagnostic image at the depths is sufficiently high.

As shown in FIG. 15B, also when the setting sequence for the weighting factors WA and WC is in operation, the target T is drawn at the depths of the diagnostic image. This indicates that even when the setting sequence for the weighting factors WA and WC is in operation, the sensitivity of the diagnostic image at the depths is kept high provided that the diagnostic image at the depths has sufficiently high sensitivity from the first.

The experiment shows that the ultrasonic diagnostic scanner of the embodiment is constructed such that the optimum weighting factors WA and WC can be set even if the attenuation differs depending on the subject and region.

Operation of the Embodiment

The third image signal SD of this embodiment is generated by multiplying the first image signal SA that reflects the fundamental component by the weighting factor WA, and multiplying the second image signal SC that reflects the harmonic component by the weighting factor WC, and adding them. The weighting factor WA for the first image signal SA is set large at the shallow depths of the subject and small at the deep depths. The weighting factor WC for the second image signal SC is set small at the shallow depths and large at the deep depths.

Thus, the diagnostic image generated from the third image signal SD reflects the harmonic component more at the shallow depth of the subject and reflects the fundamental component more at the deep depths. This provides ultrasonic images with sufficient sensitivity even at the deep depths of the subject, thus allowing the entire images to be provided with sufficient sensitivity for a diagnosis.

Moreover, the weighting factors WA and WC are automatically calculated from the noise gain GN generated from the noise signal that reflects white noise and the signal gain GC generated from the second image signal SC that reflects the harmonic component.

Accordingly, even if frequency-dependence attenuation varies depending on the subject or the region of the subject, the optimum weighting factors WA and WC for the subject or the region are surely set, thus allowing high-quality diagnostic images to be provided without influence by the difference of the subject or region.

Since the shallow depths of the subject are imaged according to the harmonic component, the occurrence of artifacts is remarkably reduced in comparison with imaging using only the fundamental component.

The ultrasonic diagnostic scanner of the embodiment can always provide high-quality diagnostic images irrespective of the subject or region because it has less artifacts and sufficient sensitivity even at the depths.

The main body 20 of this embodiment has the input section 36 for starting the setting sequence for the weighting factors WA and WC. This greatly facilitates switching of the quality of diagnostic images, thus reducing the work load on the operator.

This embodiment uses an adding process by the first adder 23 to obtain the first echo signal EA that reflects the fundamental component and the third echo signal EC that reflects the harmonic component. However, the invention is not limited to that. The way therefor is not limited at all provided that the first echo signal EA that reflects the fundamental component and the third echo signal EC that reflects the harmonic component are obtained from the echo signals received by the transmitter receiver 21. For example, in place of the first adder 23, the invention may use a first filter that allows only the fundamental component to pass through and a second filter that allows only the harmonic component to pass through from the echo signals received by the transmitter receiver 21.

Seventh Embodiment

The seventh embodiment will be described with reference to FIG. 16.

FIG. 16 is a flowchart for a diagnostic-image generation process in a case where the setting sequence for the weighting factors WA and WC in the seventh embodiment is in operation.

As shown in FIG. 16, the diagnostic-image generation process of the embodiment has steps S9 to S13, as indicated by the chain double-dashed line, added to the middle of steps S7 and S8 of the display sequence of the first embodiment.

Specifically, when a third image signal SD has been generated (step S7), the transmitter receiver 21 performs reception of one frame without transmission (step S9) to generate a noise signal of one frame which reflects white noise. The generated noise signal is sent to the gain controlling section 42, where a noise gain GN is calculated (step S10).

The transmitter receiver 21 then transmits and receives one frame to the subject (step S11) to generate a third image signal SD of one frame. The generated third image signal SD is sent to the gain controlling section 42, where a signal gain (third gain) GD is calculated (step S12).

Note that, in the first embodiment, the signal gain GC is calculated from the second image signal SC that reflects the harmonic component but, in this embodiment, the signal gain GD is calculated from the third image signal SD composed of the harmonic component and the fundamental component.

When the noise gain GN and the signal gain GD have been calculated, a display gain G best suited to displaying the diagnostic image is set based on the noise gain GN and the signal gain GD (step S13).

Specifically, in the diagnostic-image generation process of the embodiment, the display gain G best suited to displaying the diagnostic image is set by the gain controlling section 42 before the third image signal SD is displayed on the display monitor 33. In other words, in this embodiment, the display gain G is optimized after the fundamental component has been blended to the harmonic component. Accordingly, the diagnostic image displayed on the display monitor 33 becomes very clear without white noise.

Eighth Embodiment

An eighth embodiment will be described with reference to FIG. 17.

FIG. 17 is a table showing the concept of the eighth embodiment of the invention.

In this embodiment, a memory (not shown) in the main body 20 stores the table shown in FIG. 17. The table shows the relation between the depths of the intersecting point P and a transmission frequency, reception frequency, display depth, and dynamic range best suited to the respective depths.

When the intersecting point P is detected during an ultrasonic diagnosis, the table stored in the memory is referred to, from which a transmission frequency, reception frequency, display depth, and dynamic range best suited to the depth of the intersecting point P is selected. This allows an ultrasonic diagnosis under the conditions best suited to the subject or region, allowing a remarkably high-quality diagnostic image to be displayed on the display monitor 33.

The conditions for the intersecting point P are transmission frequency, reception frequency, display depth, and dynamic range. However, the invention is not limited to those; for example, the conditions may include a receiving-filter characteristic, transmission sound pressure, host-process curve, display width, display frequency, the number of transmission beams, the number of reception beams, the number of simultaneous reception beams, image processing factor, transmission waveform, and the number of transmission waves.

It is to be understood that the invention is not limited to the above-described embodiments but may be modified without departing from the sprit and scope of the invention. The combination and arrangement of components disclosed in the foregoing embodiments may be changed variously; for example, some of the components may be omitted or the components of different embodiments may be combined as appropriate.

What is claimed is:

1. An ultrasonic diagnostic scanner comprising:
   an ultrasound probe that transmits a first ultrasonic wave and a second ultrasonic wave, and receives a first reflected wave corresponding to the first ultrasonic wave and a second reflected wave corresponding to the second ultrasonic wave, for each of a plurality of scan lines, the first ultrasonic wave and the second ultrasonic wave being inverted in phase from each other, and each of the plurality of scan lines extending in a depth direction from a surface of a subject toward an interior of the subject;
   processing circuitry:
   that obtains first echo signals corresponding to respective positions in the depth direction based on the first reflected wave and second echo signals corresponding to the respective positions based on the second reflected wave, for each of the plurality of scan lines, the first echo signals and the second echo signals each including a fundamental component and a harmonic component;
   that obtains third echo signals for each of the plurality of scan lines by adding together the first and second echo signals for the respective positions, the third echo signals each reflecting the harmonic component;
   that obtains first image signals from the first echo signals and that obtains second image signals from the third echo signals;
   that applies first weighting factors to the first image signals and second weighting factors to the second image signals, for the respective positions, the first weighting factors and the second weighting factors being input from a table;
   wherein in the table, one of the first weighting factors applied to a first of the first image signals corresponding to a deeper position than a position of an intersection of a noise gain curve and a signal gain curve is greater than one of the second weighting factors applied to a first of the second image signals corresponding to the deeper position, and one of the first weighting factors applied to a second of the first image signals corresponding to a shallower position than the position of the intersection is less than one of the second weighting factors applied to a second of the second image signals corresponding to the shallower position, and
   wherein intensities of white noises multiplied by gains defined by the noise gain curve for the respective position are constant in the depth direction, and intensities of the third echo signals multiplied by gains defined by the signal gain curve for the respective position are constant in the depth direction; and
   that generates composite signals from the first image signals weighted with the first weighting factors and the second image signals weighted with the second weighting factors; and
   an image display that displays an image based on the composite signals.

2. The ultrasonic diagnostic scanner according to claim 1, wherein:
   the first and second ultrasonic waves include a first frequency component and a second frequency component higher than the first frequency component; and
   the processing circuitry obtains the harmonic component based on the third echo signal containing a difference-tone component of the first and second frequency components.

3. A method for processing an ultrasonic signal, the method comprising:
   transmitting, by an ultrasound probe, a first ultrasonic wave and a second ultrasonic wave, and receiving a first reflected wave corresponding to the first ultrasonic wave and a second reflected wave corresponding to the second ultrasonic wave, for each of a plurality of scan lines, the first ultrasonic wave and the second ultrasonic wave being inverted in phase from each other, and each of the plurality of scan lines extending in a depth direction from a surface of a subject toward an interior of the subject,
   obtaining first echo signals corresponding to respective positions in the depth direction based on the first reflected wave and second echo signals corresponding to the respective positions based on the second reflected wave, for each of the plurality of scan lines, the first echo signals and the second echo signals each including a fundamental component and a harmonic component;
   obtaining third echo signals for each of the plurality of scan lines by adding together the first and second echo signals for the respective positions, the third echo signals each reflecting the harmonic component;
   obtaining first image signals from the first echo signals and obtaining second image signals from the third echo signals;
   applying first weighting factors to the first image signals and second weighting factors to the second image signals, for the respective positions, the first weighting factors and the second weighting factors being input from a table;

wherein in the table, one of the first weighting factors applied to a first of the first image signals corresponding to a deeper position than a position of an intersection of a noise gain curve and a signal gain curve is greater than one of the second weighting factors applied to a first of the second image signals corresponding to the deeper position, and one of the first weighting factors applied to a second of the first image signals corresponding to a shallower position than the position of the intersection is less than one of the second weighting factors applied to a second of the second image signals corresponding to the shallower position, and wherein intensities of white noises multiplied by gains defined by the noise gain curve for the respective position are constant in the depth direction, and intensities of the third echo signals multiplied by gains defined by the signal gain curve for the respective position are constant in the depth direction; and generating composite signals from the first image signals weighted with the first weighting factors and the second image signals weighted with the second weighting factors; and displaying an image based on the composite signal.

4. The method for processing an ultrasonic signal according to claim 3, wherein:

the first and second ultrasonic waves include a first frequency component and a second frequency component higher than the first frequency component; and further comprising obtaining the harmonic component based on the third echo signal containing a difference-tone component of the first and second frequency components.

* * * * *